(12) United States Patent
Yamauchi et al.

(10) Patent No.: US 10,816,319 B2
(45) Date of Patent: Oct. 27, 2020

(54) MEASUREMENT APPARATUS AND MEASUREMENT METHOD

(71) Applicant: HAMAMATSU PHOTONICS K.K., Hamamatsu-shi, Shizuoka (JP)

(72) Inventors: Toyohiko Yamauchi, Hamamatsu (JP); Osamu Yasuhiko, Hamamatsu (JP); Hidenao Yamada, Hamamatsu (JP); Hisayuki Matsui, Hamamatsu (JP)

(73) Assignee: HAMAMATSU PHOTONICS K.K., Hamamatsu-shi, Shizuoka (JP)

( * ) Notice: Subject to any disclaimer, the term of this patent is extended or adjusted under 35 U.S.C. 154(b) by 0 days.

(21) Appl. No.: 16/561,059

(22) Filed: Sep. 5, 2019

(65) Prior Publication Data
US 2020/0080833 A1 Mar. 12, 2020

(30) Foreign Application Priority Data
Sep. 11, 2018 (JP) .................. 2018-169424

(51) Int. Cl.
*G01B 9/02* (2006.01)
*G01N 21/64* (2006.01)
*G01N 33/50* (2006.01)

(52) U.S. Cl.
CPC ....... *G01B 9/0203* (2013.01); *G01B 9/02087* (2013.01); *G01N 21/6456* (2013.01); *G01N 33/5005* (2013.01)

(58) Field of Classification Search
CPC ........... G01N 21/6456; G01N 21/8422; G01N 33/5005; G01B 11/06; G01B 11/0675; G01B 9/02029; G01B 9/0203; G01B 9/02087; G01B 9/0209
See application file for complete search history.

(56) References Cited

U.S. PATENT DOCUMENTS

2015/0198795 A1* 7/2015 Yamauchi .......... G02B 21/0076
359/385

FOREIGN PATENT DOCUMENTS

WO WO-2016/121250 A1 8/2016

OTHER PUBLICATIONS

Paul Held, Ph.D., et al., "Analysis of Nuclear Stained Cells, Using the Cytation TM3 Cell Imaging Multi-mode Microplate Reader with DAPI-Stained Cells," BioTek Instruments, Inc., Application Note, Cell Imaging, Rev. Apr. 10, 2013, pp. 1-9, AN041013_13.

* cited by examiner

Primary Examiner — Tarifur R Chowdhury
Assistant Examiner — Jonathon Cook
(74) Attorney, Agent, or Firm — Faegre Drinker Biddle & Reath LLP

(57) ABSTRACT

A measurement apparatus includes an interference image acquisition unit, a fluorescence image acquisition unit, an operation unit, and a timing control circuit. The operation unit generates an optical thickness image based on an interference image acquired by the interference image acquisition unit, generates a mask image showing a region in which pixel values in a fluorescence image acquired by the fluorescence image acquisition unit are larger than a threshold value, and determines an integrated value of an optical thickness in the region shown by the mask image in the optical thickness image.

9 Claims, 11 Drawing Sheets

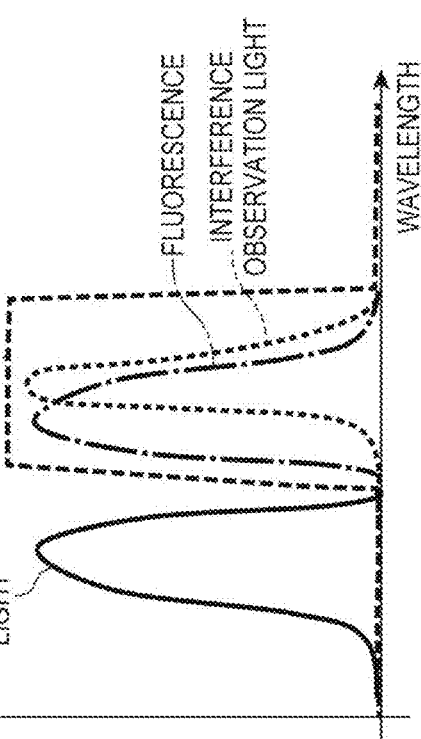
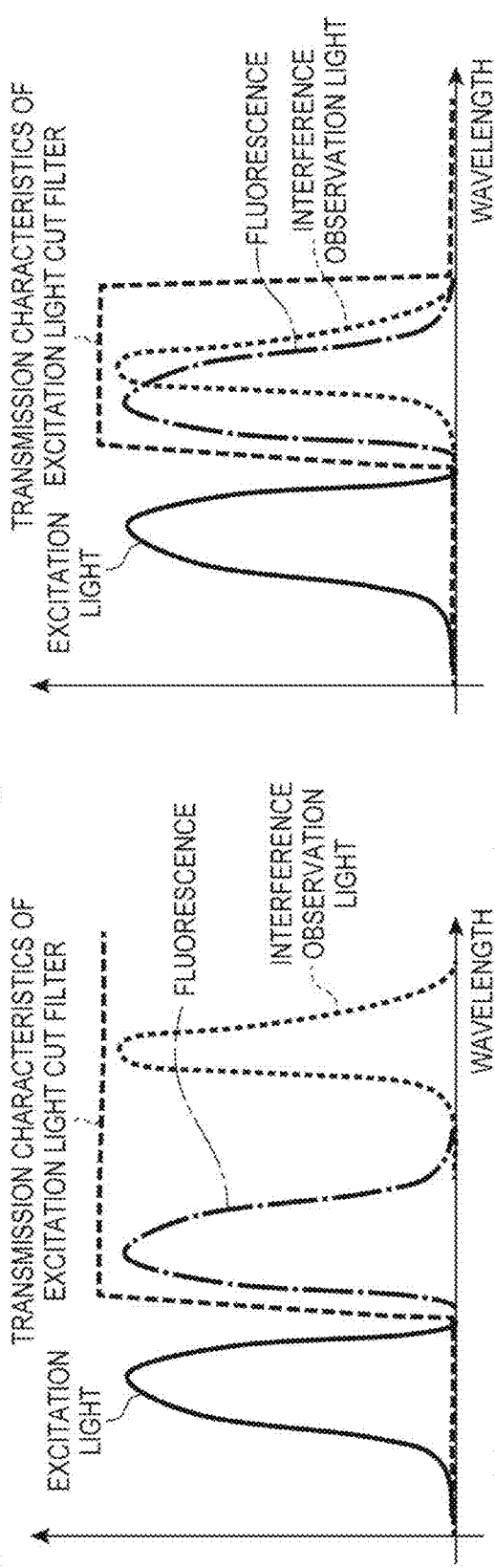
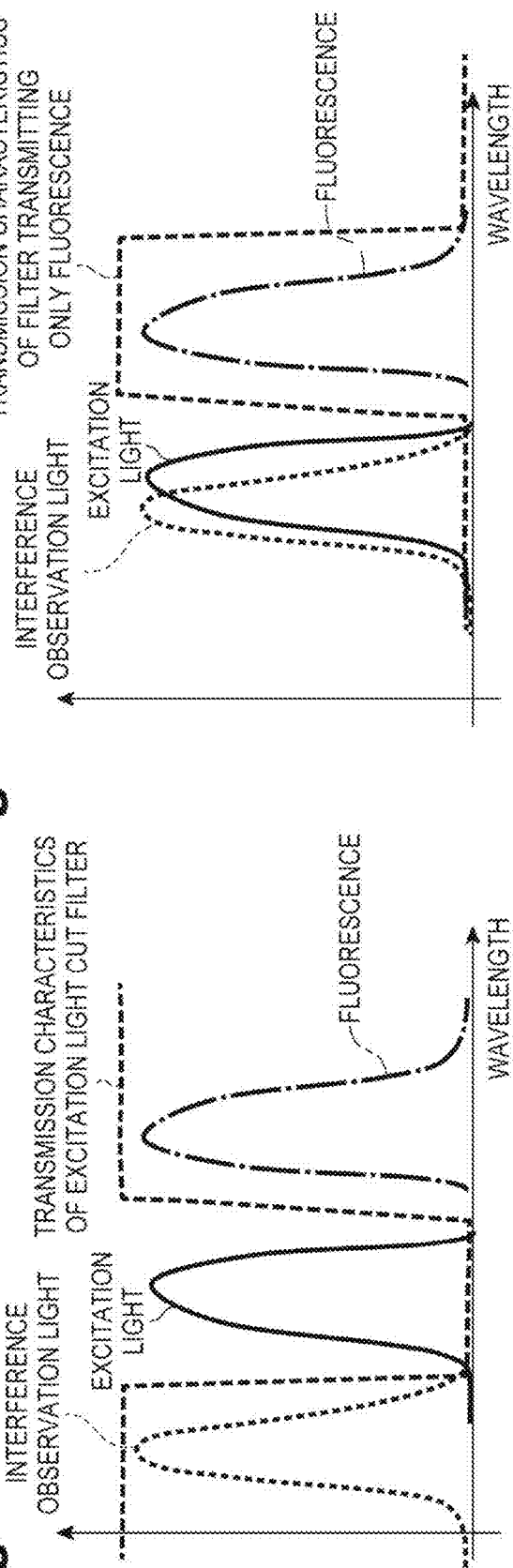

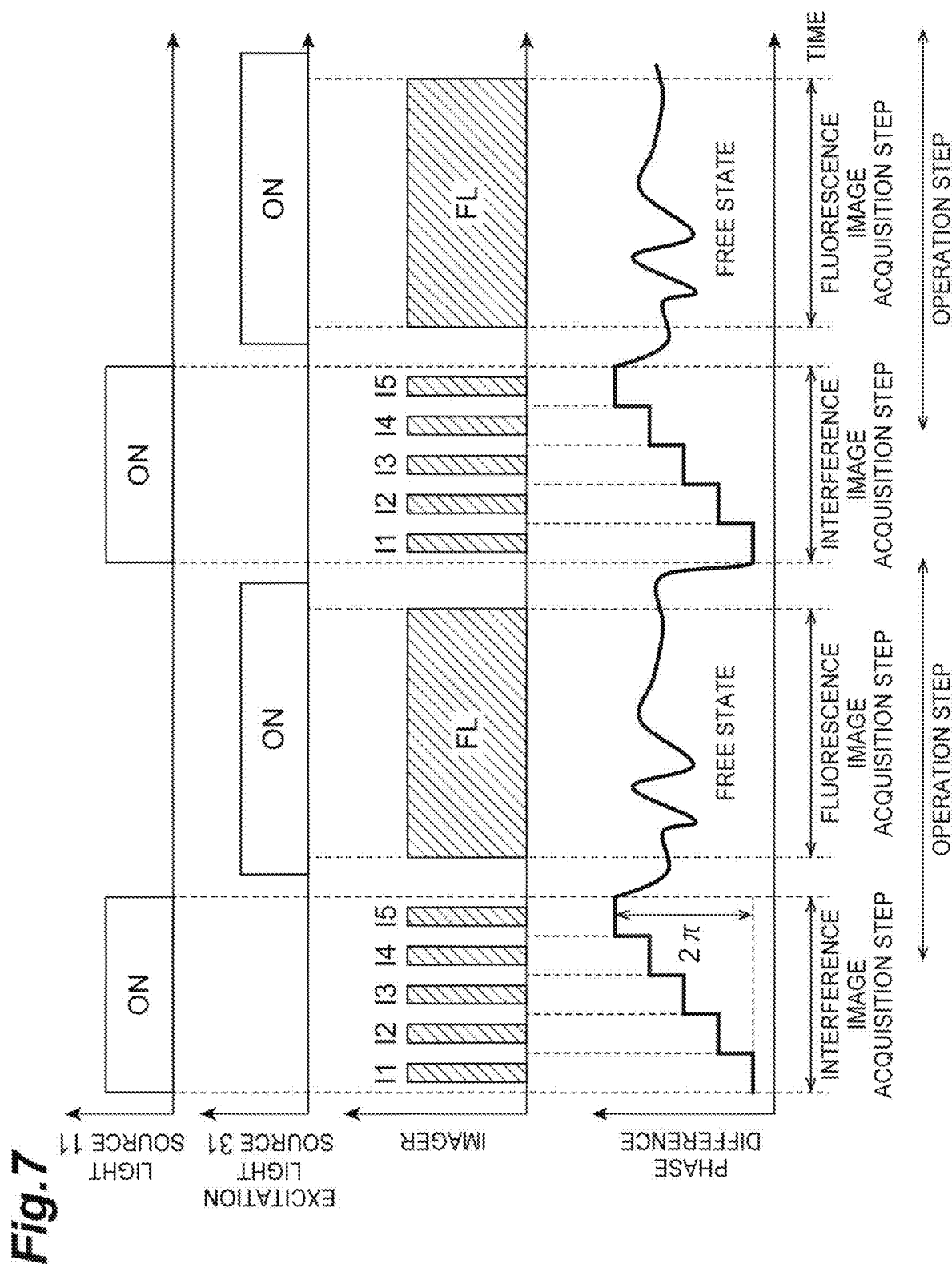

MEASUREMENT APPARATUS AND MEASUREMENT METHOD

TECHNICAL FIELD

The present disclosure relates to a measurement apparatus and a measurement method.

BACKGROUND

It is requested to accurately measure the total amount of deoxyribonucleic acid (DNA) contained in a biological sample taken from a subject in vitro. The amount to be measured is the total amount of DNA contained in a biological sample (for example, cells in a liquid in a test tube or cells seeded in a culture dish). A portion extracted from an entire sample at a certain ratio x is observed or measured, the total amount of DNA contained in the portion is divided by the extraction ratio x, and thus, the total amount of DNA contained in the entire sample can be determined.

As a method of measuring the total amount of DNA contained in the sample, there are an absorption method and a fluorescence method. In the absorption method, light at the absorption wavelength of DNA is applied to a sample, the light absorption amount in the sample is measured, and the total amount of DNA in the sample can be determined from the absorption amount by the Beer-Lambert law. In the fluorescence method, DNA in the sample is specifically stained fluorescently, the intensity of fluorescence generated when excitation light is applied to the sample is measured, and the total amount of DNA in the sample can be determined from the fluorescence intensity.

Further, since the amount of DNA contained in one cell nucleus can be estimated, the region of a cell nucleus is specifically stained, the number of stained regions is counted to deter mine the number of cell nuclei contained in the sample, and further, the total amount of DNA in the sample can be determined from the number of cell nuclei (see Non Patent Document 1).

Patent Document 1: International Publication No. 2016/121250

Non Patent Document 1: Paul Held et al., "Analysis of Nuclear Stained Cells, Using the Cytation™3 Cell Imaging Multi-Mode Microplate Reader with DAPI-Stained Cells", BioTek Instruments, inc., Application Note, AN041013_13, Rev. Apr. 10, 2013, pp. 1-9 (2013)

SUMMARY

However, even in any of the entire sample and a portion of the sample, it is difficult to accurately determine the total amount of DNA contained therein. That is, in the absorption method, the measurement result is influenced by a light absorption substance other than DNA. In the fluorescence method, the measurement result is influenced by a fluorescent substance other than DNA and influenced by background light (for example, autofluorescence), and further, the staining ratio of fluorescent staining is greatly varied by a slight condition. In any of the absorption method and the fluorescence method, the method can be approximately used for a thick sample, however, it is difficult to accurately measure a thin sample.

Further, in the fluorescence method, in a case where the concentration of a sample is very thick and cells are vertically laid on each other, cells present close to fluorescence excitation light along the optical axis of the excitation light absorb the excitation light. Thus, a problem arises that sufficient excitation light is not reached to cells present far from the excitation light and fluorescent values actually obtained as a result are under-evaluated compared with the actual number of cells. From these factors, it is difficult to accurately determine the total amount of DNA in the sample.

Further, in a case where the number of cell nuclei is determined by counting the number of stained regions, the following problem arises. That is, in a case where there are two divided cell nuclei that are originally one cell nucleus, the number of cell nuclei to be obtained is larger than the actual number. Conversely, in a case where there is one stained region that originally consists of two cell nuclei because these are in contact with each other or overlapped with each other, the number of cell nuclei to be obtained is smaller than the actual number. Thus, in a case where the number of stained regions is counted also, it is difficult to accurately determine the number of cell nuclei (and further the total amount of DNA).

The problems described above are also present not only in the case of determining the number of cell nuclei (and further the total amount of DNA) in a biological sample but also in the case of determining the amount of another object in a sample.

An object of an embodiment is to provide an apparatus and a method that can accurately measure the amount of object in a sample.

An embodiment is a measurement apparatus. The measurement apparatus includes (1) a fluorescence image acquisition unit configured to acquire a fluorescence image including an object, (2) an interference image acquisition unit configured to acquire an interference image including the object, and (3) an operation unit configured to perform an operation of determining an integrated value of an optical thickness based on the interference image, in a region in the interference image corresponding to a region in which pixel values in the fluorescence image are larger than a threshold value.

An embodiment is a measurement method. The measurement method includes (1) a fluorescence image acquisition step of acquiring a fluorescence image including an object by a fluorescence image acquisition unit, (2) an interference image acquisition step of acquiring an interference image including the object by an interference image acquisition unit, and (3) an operation step of performing an operation of determining an integrated value of an optical thickness based on the interference image, in a region in the interference image corresponding to a region in which pixel values in the fluorescence image are larger than a threshold value.

According to the embodiment, the amount of object in a sample can be accurately measured.

The present invention will be more fully understood from the detailed description given hereinbelow and the accompanying drawings, which are given by way of illustration only and are not to be considered as limiting the present invention.

Further scope of applicability of the present invention will become apparent from the detailed description given hereinafter. However, it should be understood that the detailed description and specific examples, while indicating preferred embodiments of the invention, are given by way of illustration only, since various changes and modifications within the spirit and scope of the invention will be apparent to those skilled in the art from this detailed description.

BRIEF DESCRIPTION OF THE DRAWINGS

FIG. 6A to FIG. 6D are diagrams illustrating examples of a relationship between wavelength ranges of interference observation light, excitation light, and fluorescence, and illustrate (A) a case where the wavelength range of the interference observation light is longer than the wavelength range of the fluorescence, (B) a case where the wavelength range of the interference observation light is partially overlapped with the wavelength range of the fluorescence, (C) a case where the wavelength range of the interference observation light is shorter than the wavelength range of the excitation light, and (D) a case where the wavelength range of the interference observation light is partially overlapped with the wavelength range of the excitation light.

FIG. 7 is a timing chart illustrating an operation of the measurement apparatus and a measurement method.

DETAILED DESCRIPTION

Hereinafter, embodiments of a measurement apparatus and a measurement method will be described in detail with reference to the accompanying drawings. In the description of the drawings, the same elements will be denoted by the same reference signs, without redundant description. The present invention is not limited to these examples.

Figure 1:
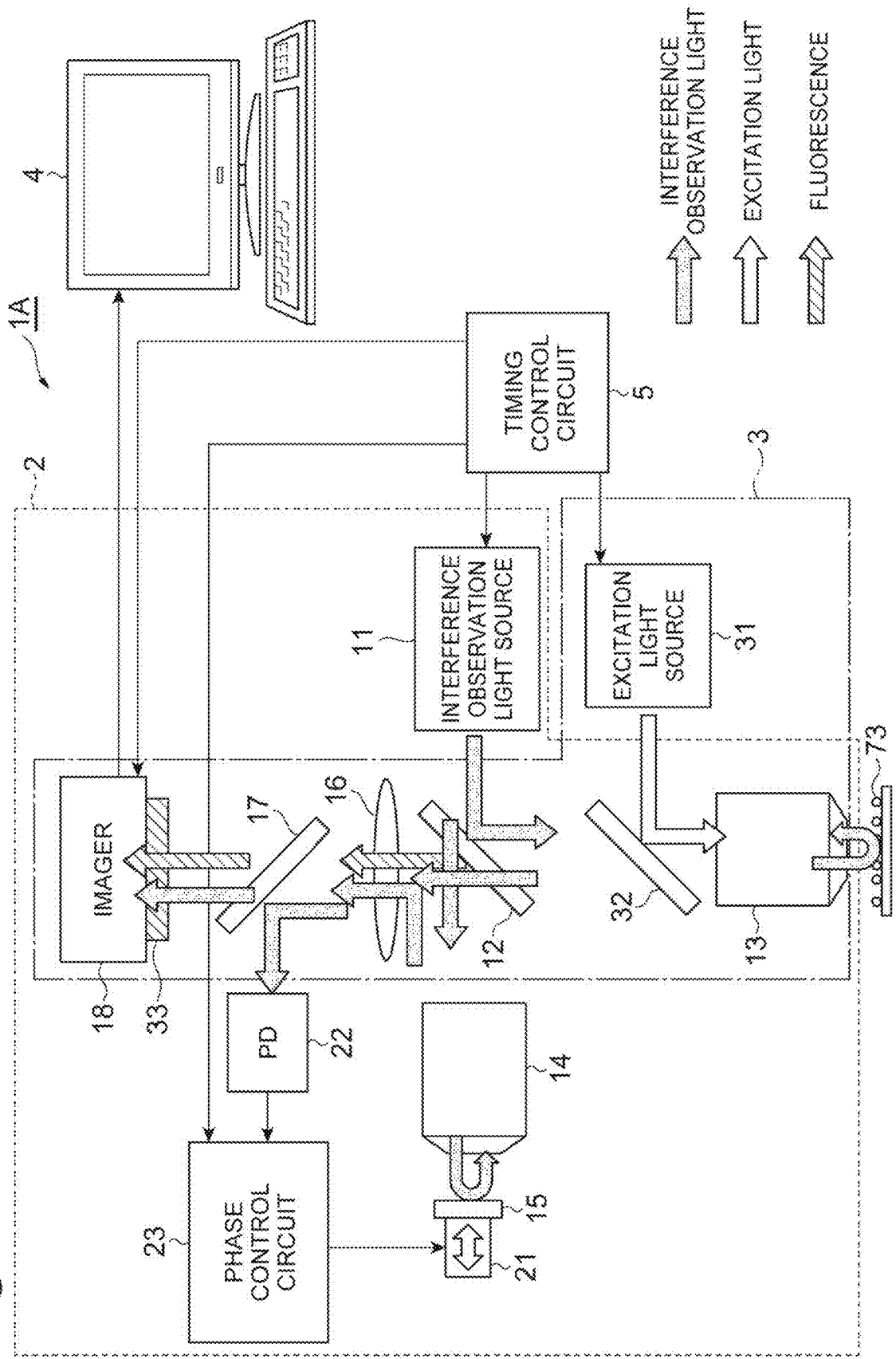
FIG. 1 is a diagram illustrating a configuration of a measurement apparatus.

FIG. 1 is a diagram illustrating a configuration of a measurement apparatus 1A. The measurement apparatus 1A includes an interference image acquisition unit 2, a fluorescence image acquisition unit 3, an operation unit 4, and a timing control circuit 5. The optical systems of the interference image acquisition unit 2 and the fluorescence image acquisition unit 3 are partially configured in common. The interference image acquisition unit 2 includes a light source 11, a beam splitter 12, an objective lens 13, an objective lens 14, a reference mirror 15, a tube lens 16, a beam splitter 17, an imager 18, a piezoelectric element 21, a photodetector 22, and a phase control circuit 23. The fluorescence image acquisition unit 3 includes an excitation light source 31, a beam splitter 32, the tube lens 16, an excitation light cut filter 33, and the imager 18.

The interference image acquisition unit 2 has a Michelson interferometer as a two-beam interferometer, and acquires an interference image of one or a plurality of objects. The fluorescence image acquisition unit 3 acquires a fluorescence image of the object. The operation unit 4 performs an operation of determining an integrated value of an optical thickness based on the interference image, in a region in the interference image corresponding to a region in which pixel values in the fluorescence image are larger than a threshold value. Preferably, the operation unit 4 generates an optical thickness image based on the interference image, generates a mask image showing the region in which the pixel values in the fluorescence image are larger than the threshold value, and determines the integrated value of the optical thickness in the region shown by the mask image in the optical thickness image.

The timing control circuit 5 controls light output timings of the light source 11 and the excitation light source 31 and an exposure timing of the imager 18, and thus, controls respective timings of interference image acquisition by the interference image acquisition unit 2 and fluorescence image acquisition by the fluorescence image acquisition unit 3.

The object is substantially transparent at the wavelength of light output from the light source 11, and is stained fluorescently. The object is not limited to a specific cell or a biological sample. Examples of the object include a cultured cell, an immortalized cell, a primary cultured cell, a cancer cell, a fat cell, a liver cell, a cardiac muscle cell, a nerve cell, a glia cell, a somatic stem cell, an embryonic stem cell, a pluripotential stem cell, an iPS cell, and a cell aggregation (a colony or spheroid) generated based on the cells, and further, a cell nucleus contained in these cells. The object is not limited to a living body.

Figure 2:
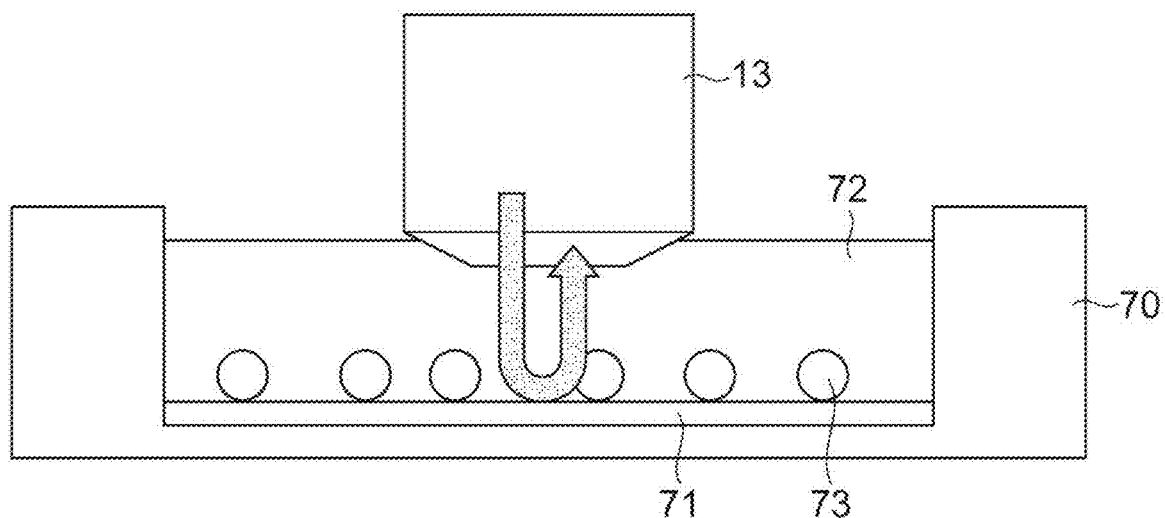
FIG. 2 is a diagram illustrating a configuration of a sample.

In the following description of the present embodiment, as an configuration example of the sample illustrated in FIG. 2, assuming that the object is a cell nucleus 73 stained fluorescently in a liquid 72 placed in a container 70. On the inner side of the bottom portion of the container 70, a reflection enhancing coating 71 is provided. A cell membrane is dissolved with a weak surfactant agent by nuclear fraction, and only cell nuclei can be extracted by centrifugation.

The light source 11 outputs interference observation light. Preferably, the light source 11 outputs incoherent light. Examples of the light source 11 include a lamp light source such as a halogen lamp, a light emitting diode (LED) light source, a super luminescent diode (SLD) light source, and an amplified spontaneous emission (ASE) light source.

The beam splitter 12 is optically coupled to the light source 11, and constitutes a Michelson interferometer as a two-beam interferometer. The beam splitter 12 may be a half mirror, for example, in which the ratio of the reflectance and the transmittance is 50:50. The beam splitter 12 splits the light output from the light source 11 into two light beams to form first split light and second split light. The beam splitter 12 outputs the first split light to the objective lens 13, and outputs the second split light to the objective lens 14.

Further, the beam splitter 12 receives the first split light reflected by the reflection enhancing coating 71 through the objective lens 13, and receives the second split light reflected by the reference mirror 15 through the objective lens 14. Then, the beam splitter 12 combines the first split light and the second split light incident thereon, and outputs interference light to the tube lens 16.

The objective lens 13 is optically coupled to the beam splitter 12, and focuses the first split light output from the beam splitter 12 to the cell nucleus 73 in the container 70. Further, the objective lens 13 receives the first split light reflected by the reflection enhancing coating 71, and outputs the first split light to the beam splitter 12.

On the optical path of the first split light between the beam splitter 12 and the objective lens 13, the beam splitter 32 is provided. The beam splitter 32 is optically coupled to the excitation light source 31. The beam splitter 32 partially reflects the excitation light output from the excitation light source 31, the first split light in the light output from the light source 11, and the fluorescence generated in the cell nucleus 73 to which the excitation light is applied, and transmits the remaining parts.

The objective lens 13 focuses the excitation light reached from the beam splitter 32 to the cell nucleus 73 in the container 70. Further, the objective lens 13 receives the fluorescence generated in the cell nucleus 73, and outputs the fluorescence to the beam splitter 12. The beam splitter 12 outputs the fluorescence to the tube lens 16.

The objective lens 14 is optically coupled to the beam splitter 12, and focuses the second split light output from the beam splitter 12 to the reflection surface of the reference mirror 15. Further, the objective lens 14 receives the second split light reflected by the reflection surface of the reference mirror 15, and outputs the second split light to the beam splitter 12.

The tube lens 16 is optically coupled to the beam splitter 12 constituting the interference optical system, and forms an image of the interference light and the fluorescence output from the beam splitter 12 on the imaging plane of the imager 18 through the beam splitter 17. The beam splitter 17 partially reflects the interference light and the fluorescence, and transmits the remaining parts. The ratio of the reflectance and the transmittance in the beam splitter 17 is 20:80, for example.

The imager 18 is optically coupled to the beam splitter 17, receives the interference light reached from the beam splitter 17 and acquires an interference image, and further, receives the fluorescence reached from the beam splitter 17 and acquires a fluorescence image. For example, the imager 18 is an image sensor, such as a CCD area image sensor and a CMOS area image sensor. The excitation light cut filter 33 provided in front of the light receiving plane of the imager 18 selectively transmits the interference light and the fluorescence, and selectively cuts off the excitation light.

The piezoelectric element 21 moves the reflection surface of the reference mirror 15 in the direction perpendicular to the reflection surface. The piezoelectric element 21 can adjust the optical path difference (that is, the phase difference) between the two light beams in the two-beam interferometer by moving the reflection surface. The piezoelectric element 21 can determine the position of the reflection surface of the reference mirror 15 with the resolution less than the wavelength. In the two-beam interferometer, the optical path difference between two light beams is variable.

In addition, assuming that the optical distance from the beam splitter 12 to the reflection enhancing coating 71 is L1, and the optical distance from the beam splitter 12 to the reflection surface of the reference mirror 15 is L2, the optical path difference between the two light beams of the two-beam interferometer is 2 (L1-L2). When the optical path difference is not larger than the coherent length of the output light of the light source 11, the imager 18 can acquire a clear interference image. When the center wavelength of the output light of the light source 11 is λ0, a phase difference Δϕ between the two light beams in the two-beam interferometer is expressed by the following Formula (1).

$$\Delta\phi = 2\pi \times 2 \times (L1-L2)/\lambda 0 \quad (1)$$

The photodetector 22 is optically coupled to the beam splitter 17, receives the interference light reached from the beam splitter 17, and outputs a detection signal. Examples of the photodetector 22 include a photodiode, avalanche photodiode, and photomultiplier tube, and may include a line sensor (linear sensor), CCD area image sensor, CMOS area image sensor, and any other sensor.

The phase control circuit 23 is electrically coupled to the photodetector 22, and receives the detection signal output from the photodetector 22. Further, the phase control circuit 23 is electrically coupled to the piezoelectric element 21, and controls the adjustment operation of the optical path difference by the piezoelectric element 21. The phase control circuit 23 detects the optical path difference between the two light beams in the two-beam interferometer based on the received detection signal. Then, the phase control circuit 23 controls the adjustment operation of the optical path difference by the piezoelectric element 21 by feedback control based on the detection result. Thus, a state (a locked state) can be achieved in which the optical path difference between the two light beams in the two-beam interferometer is stabilized at the set value.

The interference image acquisition unit 2 can acquire the interference image of the object (the cell nucleus 73) by imaging with the imager 18 in the locked state. The fluorescence image acquisition unit 3 can acquire the fluorescence image of the object (the cell nucleus 73) by imaging with the imager 18. The operation unit 4 determines the integrated value of the optical thickness based on the interference image in the region in the interference image corresponding to the region in which the pixel values in the fluorescence image are larger than the threshold value.

The operation unit 4 may be a computer such as a personal computer, having a memory such as a RAM and ROM, and a processor (an arithmetic circuit) such as a CPU, and a smart device. Further, the operation unit 4 may include an input unit (for example, a keyboard, a mouse, and a touch panel) that accepts inputs from an operator, and a display unit (for example, a display) that displays the interference image, the optical thickness image, and any other image. Further, the operation unit 4 preferably has functions that displays images, for example, on a screen and accepts the instruction of a region on the screen by the operator.

The operation of the interference image acquisition unit 2 is as follows. The light output from the light source 11 is split into two light beams by the beam splitter 12 to form the first split light and the second split light, and the first split light and the second split light are output from the beam splitter 12.

The first split light output from the beam splitter 12 is focused to the cell nucleus 73 in the container 70 by the objective lens 13 through the beam splitter 32, and reflected by the reflection enhancing coating 71 provided on the inner side of the bottom portion of the container 70. The first split light reflected by the reflection enhancing coating 71 is input to the beam splitter 12 through the objective lens 13 and the beam splitter 32. The second split light output from the beam splitter 12 is focused to the reflection surface of the reference mirror 15 by the objective lens 14, and reflected by the reflection surface. The second split light reflected by the reflection surface of the reference mirror 15 is input to the beam splitter 12 through the objective lens 14.

The first split light input from the objective lens 13 to the beam splitter 12 and the second split light input from the objective lens 14 to the beam splitter 12 are combined by the beam splitter 12, and the interference light is output from the beam splitter 12. The interference light is passed through the tube lens 16, then split into two beams by the beam splitter 17, and received by the imager 18 and the photodetector 22, respectively.

The detection signal is output from the photodetector 22 receiving the interference light, and the optical path difference between the two light beams in the two-beam interferometer is detected by the phase control circuit 23 based on the detection signal. Then, by feedback control on the piezoelectric element 21 by the phase control circuit 23, a state is achieved (a locked state) in which the optical path difference between the two light beams in the two-beam interferometer is stabilized at the set value. In the locked state, an interference image is acquired by the imager 18 receiving the interference light, and the interference image is output to the operation unit 4. Then, the operation unit 4 generates the optical thickness image of the object (the cell nucleus 73) based on the interference image.

The operation unit 4 generates the optical thickness image from a plurality of interference images by a phase shift method. That is, the interference image acquisition unit 2 achieves the state in which the optical path difference in the two-beam interferometer is stabilized at a plurality of set values different from each other, and acquires an interference image in each of the states. The operation unit 4 can obtain a phase image based on a plurality of interference images acquired by the interference image acquisition unit 2 (see Patent Document 1). Further, the operation unit 4 can obtain an optical thickness image from the phase image.

For example, the interference image acquisition unit 2 stabilizes the phase difference of the interference light in a certain initial phase by feedback control using the piezoelectric element 21, the photodetector 22, and the phase control circuit 23, and acquires an interference image I1 by the imager 18 in the state in which the phase difference is stabilized. Subsequently, the interference image acquisition unit 2 stabilizes the phase difference of the interference light in "the initial phase+π/2" using the piezoelectric element 21, the photodetector 22, and the phase control circuit 23, and acquires an interference image I2 by the imager 18 in the state in which the phase difference is stabilized. Similarly, the interference image acquisition unit 2 acquires an interference image I3 by the imager 18 in the state in which the phase difference of the interference light is stabilized in "the initial phase+π", acquires an interference image I4 by the imager 18 in the state in which the phase difference of the interference light is stabilized in "the initial phase+3π/2", and acquires an interference image I5 by the imager 18 in the state in which the phase difference of the interference light is stabilized in "the initial phase+2π".

The operation unit 4 performs an operation of the following Formula (2) using these five interference images I1 to I5, and determines a phase image Φ. arg is an operator that acquires the argument of the complex number. i is the imaginary unit. After applying a phase unwrap process and a background distortion correction process to the phase image Φ, the operation unit 4 determines an optical thickness OT by the following Formula (3), and determines the optical thickness image. In addition, the parameters shown in these Formulas are the functions of the pixel position (x, y), and the operations of these Formulas are performed for each pixel.

$$\Phi = \arg\{(I1 - 2 \times I3 + I5) + i(2 \times I2 - 2 \times I4)\} \quad (2)$$

$$OT = \Phi \times \frac{\lambda 0}{4\pi} \quad (3)$$

For background correction, a polynomial function (for example, a Zernike polynomial) where x and y are variables is used, and thus, an excellent (flat) background can be obtained. Further, in a case where the spatial frequency of the distortion component in the background is sufficiently lower than the spatial frequency of individual samples, a high-pass filtering process can also be applied. The flatness in the background of the optical thickness image is preferably less than 5 nm in the standard deviation of the optical thickness.

The optical thickness OT expresses the amount of the phase change given to the light transmitted through the sample. The optical thickness OT is given by the following Formula (4), where the thickness of the cell nucleus 73 is d, the average refractive index of the cell nucleus 73 is $n_c$, and the refractive index of the liquid 72 is $n_m$.

$$OT = d \times (n_c - n_m) \quad (4)$$

The operation of the fluorescence image acquisition unit 3 is as follows. The excitation light output from the excitation light source 31 is reflected by the beam splitter 32, and focused and applied to the cell nucleus 73 in the container 70 by the objective lens 13. The fluorescence generated in the cell nucleus 73 by the application of the excitation light is received by the imager 18 through the objective lens 13, the beam splitter 32, the beam splitter 12, the tube lens 16, the beam splitter 17, and the excitation light cut filter 33. The imager 18 receiving the fluorescence can acquire a fluorescence image. The operation unit 4 inputs the fluorescence image.

Next, using FIG. 3 to FIG. 5, configurations of modifications of the measurement apparatus will be described. The configuration of the measurement apparatus (in particular, the configurations of the interference image acquisition unit and the fluorescence image acquisition unit) can be modified in various forms. In addition, in FIG. 3 to FIG. 5 illustrating the configurations of the modifications, the operation unit and the timing control circuit are omitted, and the beam splitter 17, the photodetector 22, and the phase control circuit 23 of the interference image acquisition unit are also omitted.

Figure 3:
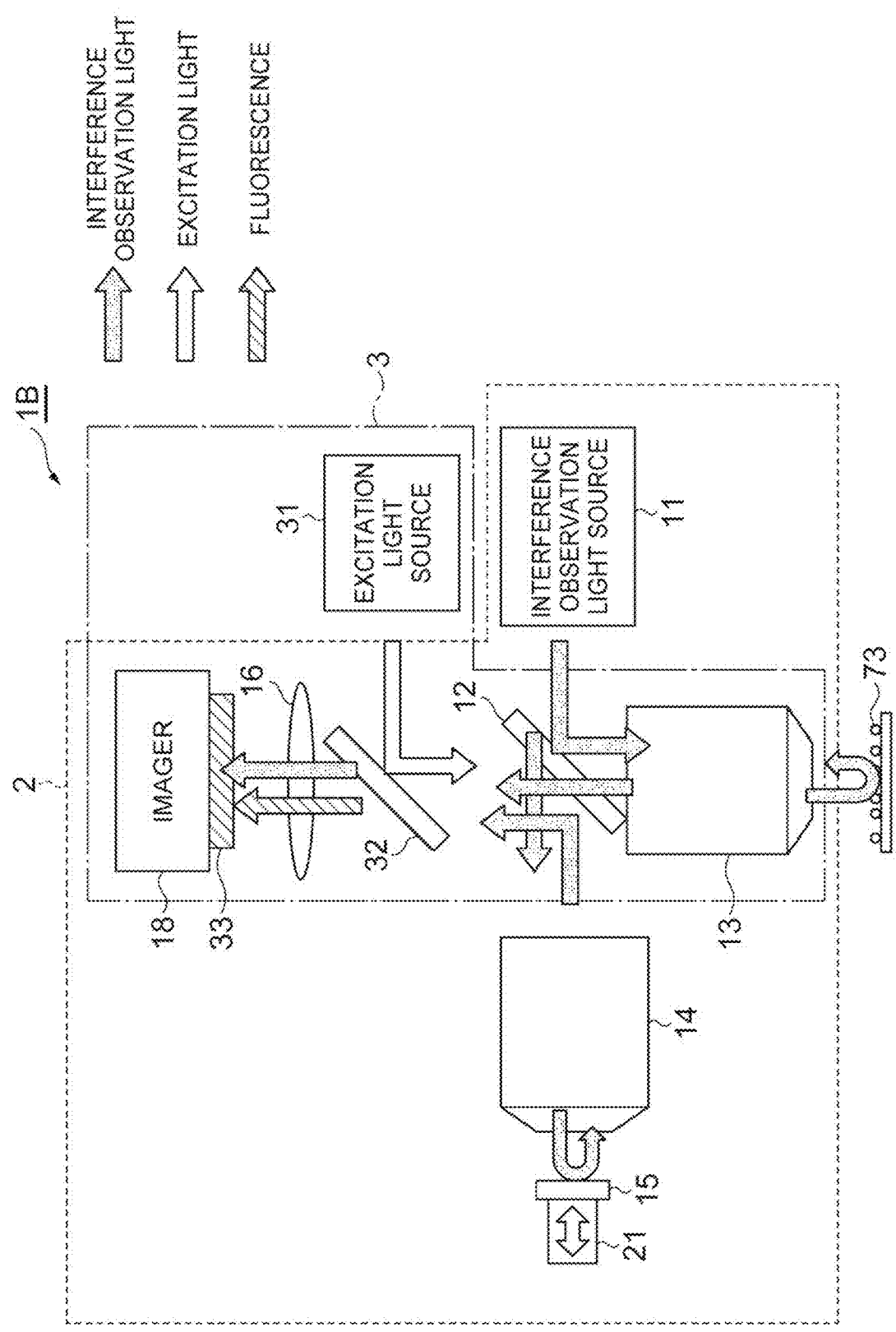
FIG. 3 is a diagram illustrating a configuration of a measurement apparatus according to a first modification.

Compared with the configuration of the measurement apparatus 1A illustrated in FIG. 1, a measurement apparatus 1B according to a first modification illustrated in FIG. 3 has configurations almost similar to the configurations of the interference image acquisition unit 2 and the fluorescence image acquisition unit 3, however, the apparatus is different in the position on which the beam splitter 32 is provided. In the measurement apparatus 1A illustrated in FIG. 1, the beam splitter 32 is provided in the two-beam interferometer, whereas in the measurement apparatus 1B of the first modification illustrated in FIG. 3, the beam splitter 32 is provided outside the two-beam interferometer on the optical path between the beam splitter 12 and the tube lens 16.

Figure 4:
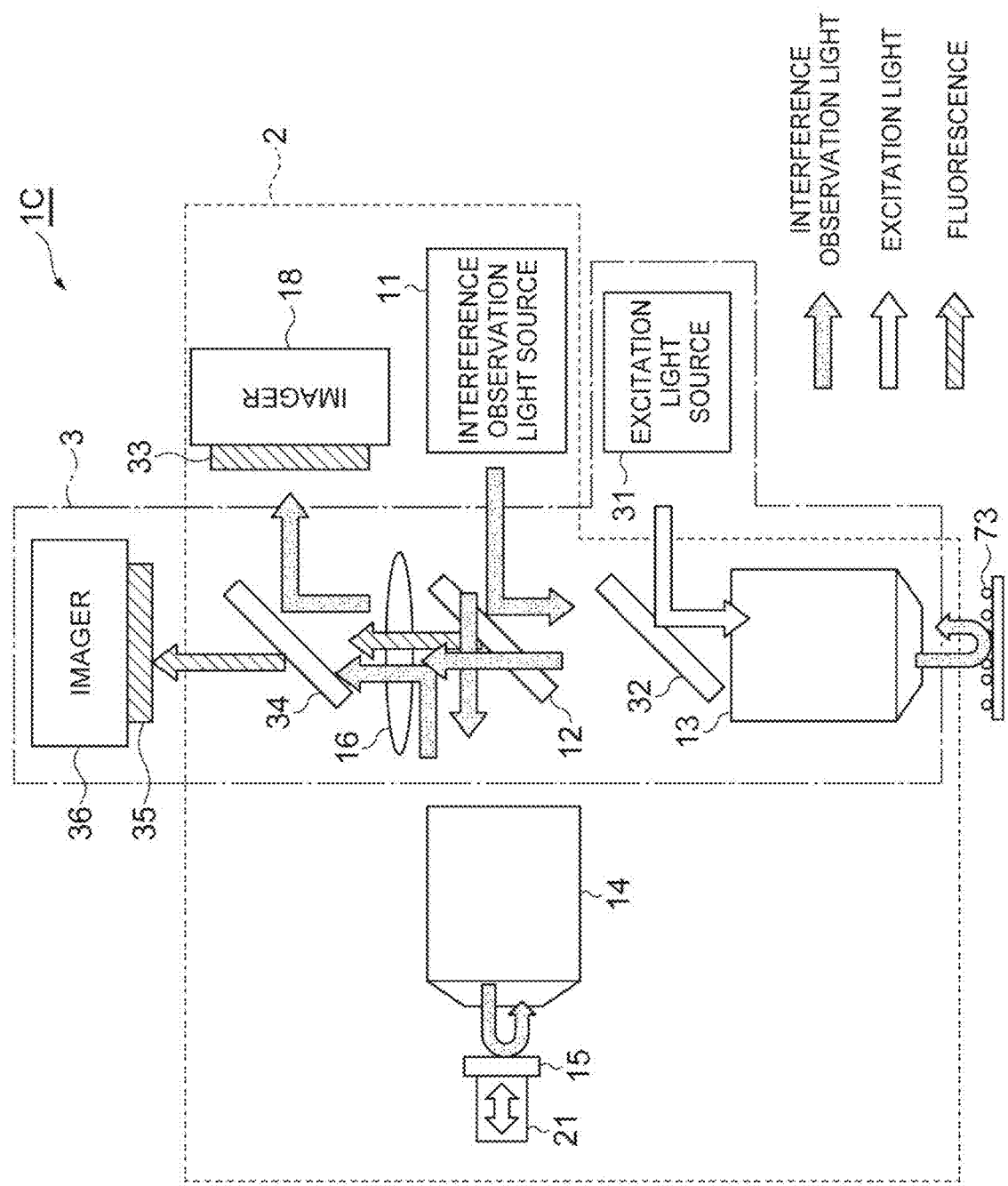
FIG. 4 is a diagram illustrating a configuration of a measurement apparatus according to a second modification.
Figure 5:
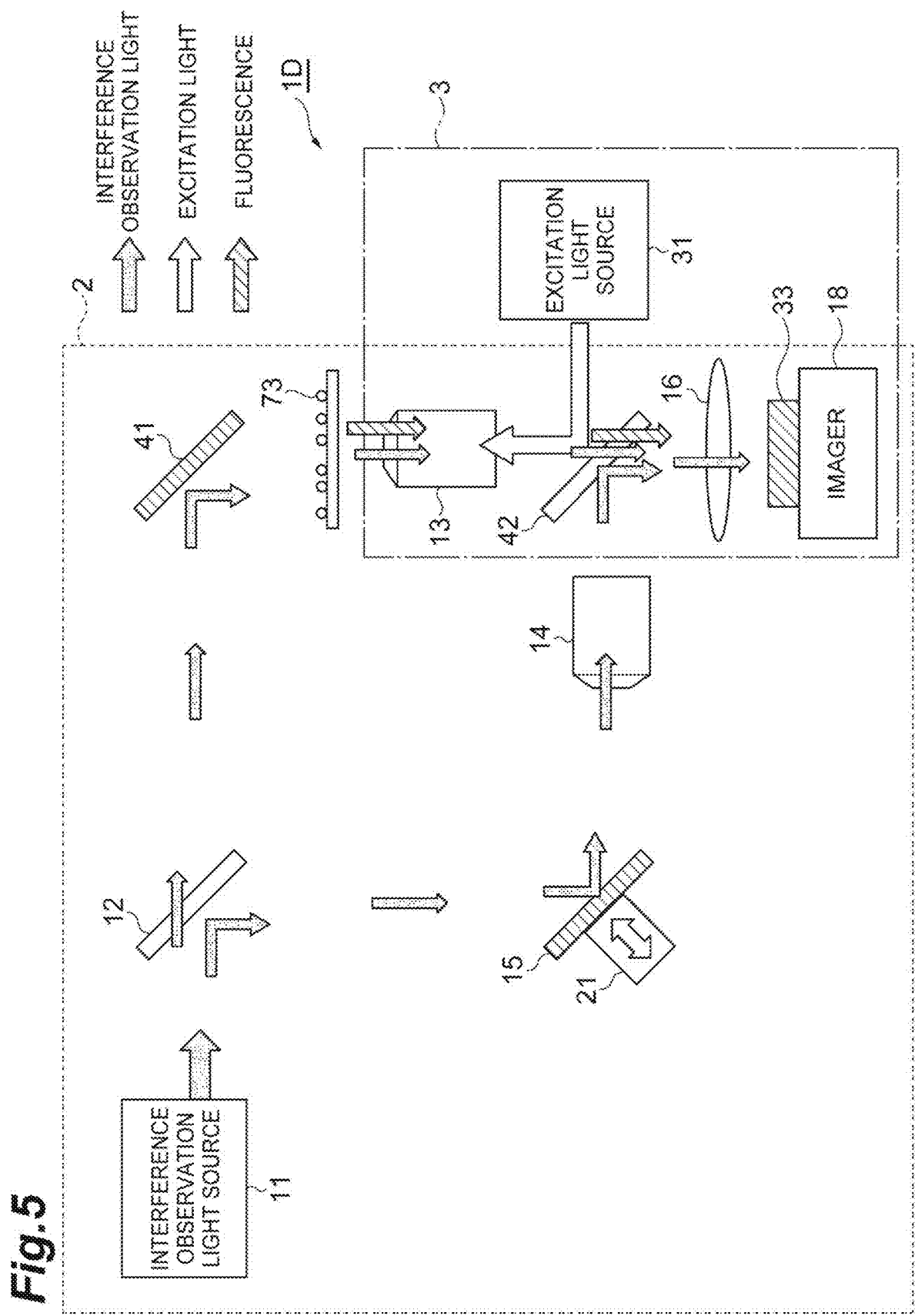
FIG. 5 is a diagram illustrating a configuration of a measurement apparatus according to a third modification.

Compared with the configuration of the measurement apparatus 1A illustrated in FIG. 1, a measurement apparatus 1C according to a second modification illustrated in FIG. 4 is different in that the apparatus further includes a dichroic mirror 34 and a fluorescence transmission filter 35, and further includes a fluorescence image acquisition imager 36 in addition to the interference image acquisition imager 18.

The dichroic mirror 34 is optically coupled to the beam splitter 12, and receives interference light and fluorescence output from the beam splitter 12. The dichroic mirror 34 selectively reflects the interference light and selectively transmits the fluorescence in the interference light and the fluorescence incident thereon. The interference image acquisition imager 18 receives the interference light reflected by the dichroic mirror 34, and acquires an interference image. The fluorescence image acquisition imager 36 receives the fluorescence transmitted through the dichroic mirror 34, and acquires a fluorescence image. The fluorescence transmission filter 35 provided in front of the light receiving plane of the imager 36 selectively transmits the fluorescence.

Compared with the configurations of the above measurement apparatuses 1A to 1C, a measurement apparatus 1D according to a third modification illustrated in FIG. 5 is different in that a Mach-Zehnder interferometer is included as a two-beam interferometer.

In the measurement apparatus 1D of the third modification, interference observation light output from the light source 11 is split into two light beams by the beam splitter 12 to form first split light and second split light, and the first split light and the second split light are output from the beam splitter 12. The first split light output from the beam splitter 12 is reflected by a mirror 41, transmitted through the cell nucleus 73, and input to a beam splitter 42 through the objective lens 13. The second split light output from the beam splitter 12 is reflected by the reference mirror 15, and input to the beam splitter 42 through the objective lens 14.

The first split light input from the objective lens 13 to the beam splitter 42 and the second split light input from the objective lens 14 to the beam splitter 42 are combined by the beam splitter 42, and interference light is output from the beam splitter 42. The interference light is received by the imager 18 through the tube lens 16. In a state (a locked state) in which the optical path difference between the two light beams in the two-beam interferometer is stabilized at the set value, the imager 18 receiving the interference light acquires an interference image, and the interference image is output to the operation unit 4. Then, the operation unit 4 determines the optical thickness image of the object (the cell nucleus 73) based on the interference image.

The excitation light output from the excitation light source 31 is reflected by the beam splitter 42, and focused and applied to the cell nucleus 73 by the objective lens 13. The fluorescence generated in the cell nucleus 73 by the application of the excitation light is received by the imager 18 through the objective lens 13, the beam splitter 42, the tube lens 16, and the excitation light cut filter 33. The imager 18 receiving the fluorescence can acquire a fluorescence image. The operation unit 4 inputs the fluorescence image.

In addition, in the configuration examples in FIG. 1, FIG. 3, FIG. 4, and FIG. 5, in some cases, the beam splitter can be used instead of the dichroic mirror, and conversely, the dichroic mirror can be used instead of the beam splitter. In the case of the beam splitter, the ratio of the reflectance and the transmittance is 20:80, for example.

In any of the configurations of the measurement apparatuses 1A to 1D, the interference observation light output from the light source 11 passes the two-beam interferometer (a Michelson interferometer or a Mach-Zehnder interferometer), also passes a cell nucleus placed on the optical path in the two-beam interferometer, and forms an interference image on the light receiving plane of the imager. Further, the fluorescence generated in the cell nucleus by the application of the excitation light output from the excitation light source 31 forms a fluorescence image on the light receiving plane of the imager. In the measurement apparatuses 1A to 1D, parts of the optical systems (in particular, the objective lens 13) of the interference image acquisition unit 2 and the fluorescence image acquisition unit 3 are configured in common, and the interference image and the fluorescence image can be acquired in almost the same field of view.

The measurement apparatuses 1A to 1D can acquire the interference image and the fluorescence image almost simultaneously. The measurement apparatus 1C of the second modification separately includes the interference image acquisition imager 18 and the fluorescence image acquisition imager 36, and thus, the interference image and the fluorescence image can be acquired simultaneously. The measurement apparatus 1C of the second modification may not include the timing control circuit.

The measurement apparatuses 1A, 1B, and 1D can alternately acquire the interference image and the fluorescence image by time division using one imager 18. Since the exposure time for imaging each of the interference image and the fluorescence image is short, the measurement apparatuses 1A, 1B, and 1D can acquire the interference image and the fluorescence image almost simultaneously. For example, it is possible that the exposure time necessary to image the fluorescence is about a few hundreds milliseconds to a few seconds, whereas the exposure time necessary to image the interference is less than 100 milliseconds. Assuming that the interference is imaged immediately after the fluorescence is imaged or the fluorescence is imaged immediately after the interference is imaged, it is thought that a large motion artifact is not generated compared with the exposure time for the fluorescence, and substantially almost simultaneous imaging can be regarded, even in the case of time division imaging.

The measurement apparatus according to the present embodiment only has to have a configuration that can acquire the interference image and the fluorescence image almost simultaneously in almost the same field of view. That is, the two-beam interferometer in the interference image acquisition unit 2 may be any of a Michelson interferometer and a Mach-Zehnder interferometer. The position at which the excitation light is introduced may be in the inside or on the outside of the two-beam interferometer. The interference image and the fluorescence image may be alternately imaged using one imager, or the interference image acquisition imager and the fluorescence image acquisition imager may be separately included.

Further, in order to acquire the interference image and the fluorescence image in almost the same field of view, the optical systems of the interference image acquisition unit and the fluorescence image acquisition unit are preferably partially configured in common, however, the interference image acquisition unit and the fluorescence image acquisition unit may not include the common part of the optical systems. Even though the interference image acquisition unit and the fluorescence image acquisition unit are separate optical systems, these units can only have to acquire the interference image and the fluorescence image in almost the same field of view.

Next, using FIG. 6A to FIG. 6D, the relationship between the wavelength range of the interference observation light output from the light source 11, the wavelength range of the excitation light output from the excitation light source 31, and the wavelength range of the fluorescence generated in the cell nucleus 73 by the application of the excitation light will be described. FIG. 6A to FIG. 6D are diagrams illustrating examples of the relationship between the wavelength ranges of the interference observation light, the excitation light, and the fluorescence. In general, the wavelength range of the fluorescence is located on the long wavelength side from the wavelength range of the excitation light.

In the example shown in FIG. 6A, the wavelength range of the interference observation light is longer than the wavelength range of the fluorescence, and apart from the wavelength range of the fluorescence to a degree that the interference observation light can be separated from the fluorescence by a spectroscopic method. In this case, the interference image and the fluorescence image can be alternately acquired by time division using one imager, or the interference image and the fluorescence image can be also preferably acquired simultaneously using two imagers.

In the example shown in FIG. 6B, the wavelength range of the interference observation light is partially overlapped with the wavelength range of the fluorescence. In this case, the interference image and the fluorescence image can be alternately acquired by time division using one imager. This is preferable because the chromatic aberration between the interference image and the fluorescence image can be minimized. However, the interference image and the fluorescence image cannot be acquired simultaneously using two imagers.

In the example shown in FIG. 6C, the wavelength range of the interference observation light is shorter than the wavelength range of the excitation light, and apart from the wavelength range of the excitation light to a degree that the interference observation light can be separated from the excitation light by a spectroscopic method. In this case, the interference image and the fluorescence image can be alternately acquired by time division using one imager, or the interference image and the fluorescence image can also be acquired simultaneously using two imagers. However, in some cases, the chromatic aberration between the interference image and the fluorescence image causes a problem, and in this case, an optical system that accurately corrects the chromatic aberration is desirably used.

In the example shown in FIG. 6D, the wavelength range of the interference observation light is partially overlapped with the wavelength range of the excitation light. In this case, the interference image and the fluorescence image can be alternately acquired by time division using one imager, however, the interference image and the fluorescence image cannot be acquired simultaneously using two imagers.

Next, using FIG. 7, the operation of the measurement apparatus according to the present embodiment and the procedures of the measurement method according to the present embodiment will be described. FIG. 7 is a timing chart describing the operation of the measurement apparatus of the present embodiment and the measurement method of the present embodiment. This drawing shows examples of the light output period of the light source 11, the excitation light output period of the excitation light source 31, the exposure period of the imager, and the time variation in the phase difference of the interference light (the phase difference between the two light beams in the two-beam interferometer).

The measurement method according to the present embodiment includes an interference image acquisition step, a fluorescence image acquisition step, and an operation step. This drawing shows an operation example in a case where the interference image acquisition step and the fluorescence image acquisition step are alternately performed by time division using one imager.

In the interference image acquisition step, the light source 11 outputs interference observation light, and the excitation light source 31 does not output excitation light. The interference image acquisition unit 2 sets the phase difference of the interference light in stages from the initial phase by $\pi/2$ by feedback control using the piezoelectric element 21, the photodetector 22, and the phase control circuit 23, and captures interference images I1 to I5 by the imager 18 in the state in which the phase difference is stabilized at the set value in each stage.

In the fluorescence image acquisition step, the light source 11 does not output interference observation light, and the excitation light source 31 outputs excitation light. The phase difference in this period is in a free state that is unstable. The fluorescence image acquisition unit 3 captures a fluorescence image FL by the imager 18.

The interference image acquisition step and the fluorescence image acquisition step are alternately repeated, and thus, the interference images I1 to I5 and the fluorescence image FL can be sequentially acquired. Further, as necessary, a configuration may be possible in which, after the interference image acquisition step and the fluorescence image acquisition step are performed for a certain field of view to acquire the interference image and the fluorescence image, a sample is moved by a motorized stage, for example, and the interference image acquisition step and the fluorescence image acquisition step are performed for another field of view to acquire the interference image and the fluorescence image. With this configuration, the interference image and the fluorescence image can be acquired for a plurality of fields of view.

In the operation step, the operation unit 4 determines the optical thickness image based on the interference images I1 to I5 acquired by the interference image acquisition unit 2 by the method described above. The operation unit 4 performs an operation of determining the integrated value of the optical thickness based on the interference image in the region in the interference image corresponding to the region in which the pixel values in the fluorescence image are larger than the threshold value.

In the operation step, the operation unit 4 performs processes described later, using the interference image and the fluorescence image acquired in the interference image acquisition step and the subsequent fluorescence image acquisition step, or using the fluorescence image and the interference image acquired in the fluorescence image acquisition step and the subsequent interference image acquisition step. The operation step may be performed in parallel with both or any one of the interference image acquisition step and the fluorescence image acquisition step.

Next, the processes (the operation step) by the operation unit 4 will be described in detail. In the operation step, the operation unit 4 performs the following operating processes using the interference image acquired by the interference image acquisition unit 2 and the fluorescence image acquired by the fluorescence image acquisition unit 3.

The operation unit 4 determines a phase image based on the above Formula (2) from a plurality of interference images acquired by the interference image acquisition unit 2, and further, determines an optical thickness image based on the above Formula (3) from the phase image. In addition, as shown in the above Formula (3), the phase value $\Phi$ and the optical thickness OT are in a proportional relationship, and thus, it can be said that the phase image and the optical thickness image are substantially equivalent to each other.

Figure 8:
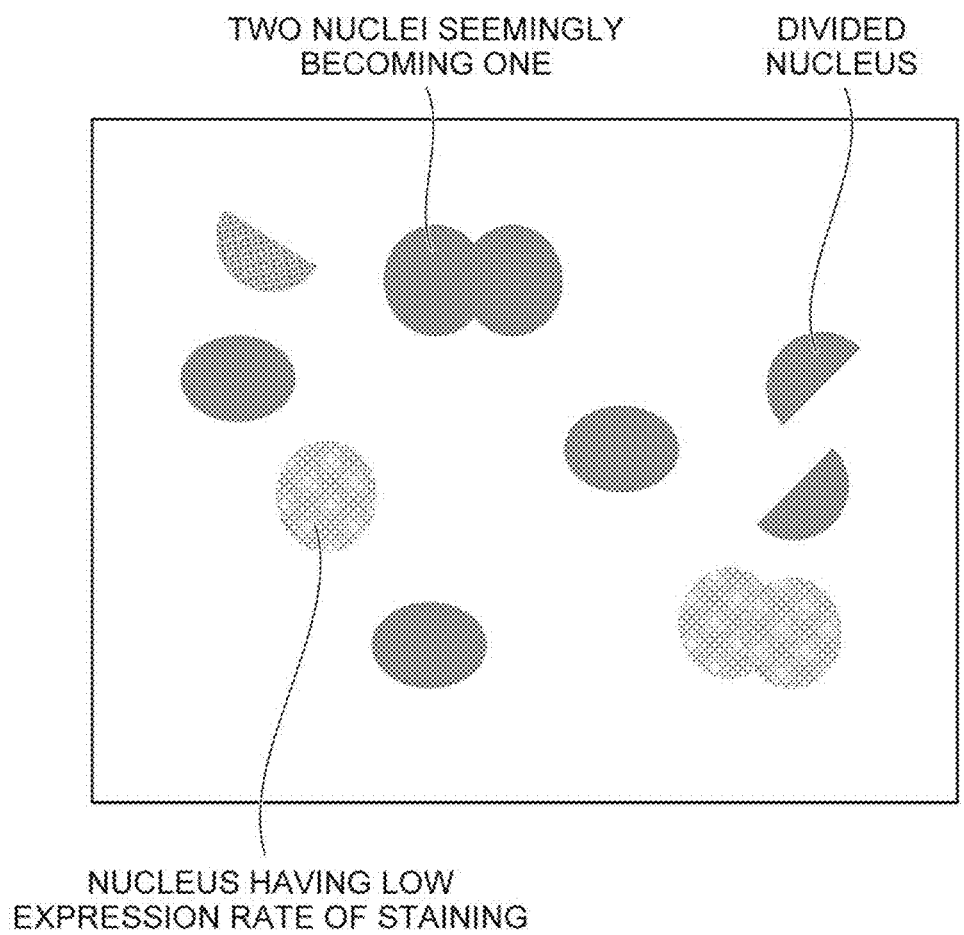
FIG. 8 is a diagram schematically showing a fluorescence image.
Figure 9:
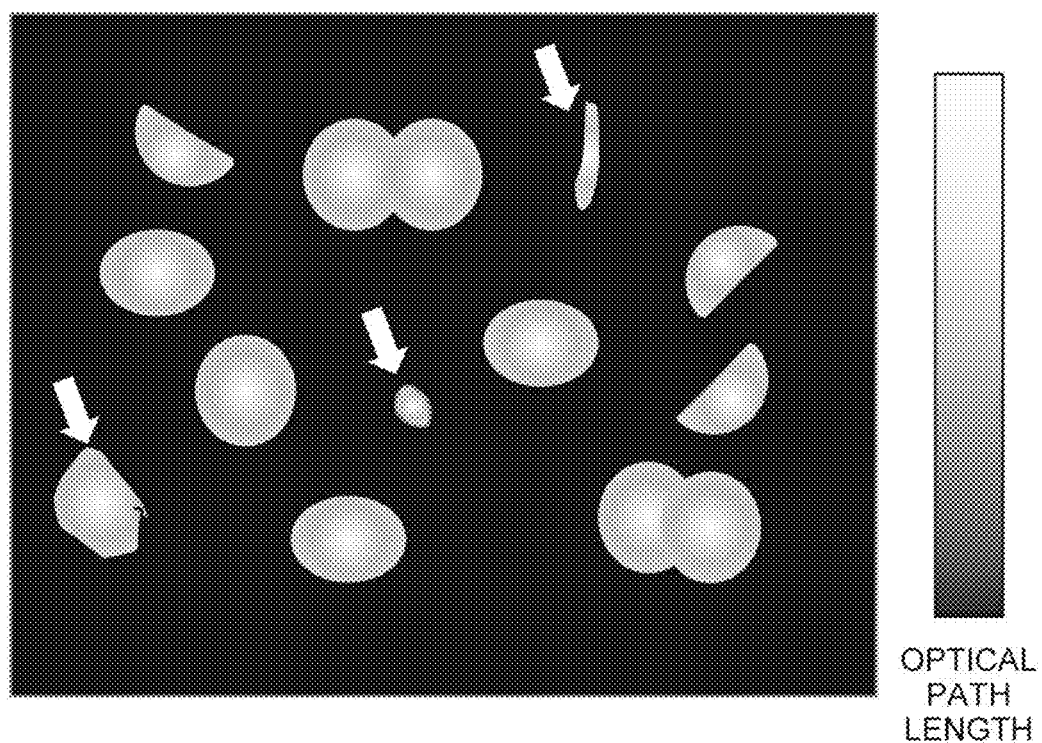
FIG. 9 is a diagram schematically showing an optical thickness image.

FIG. 8 is a diagram schematically showing a fluorescence image. FIG. 9 is a diagram schematically showing an optical thickness image. The fluorescence image and the optical thickness image are acquired by imaging substantially the same field of view for substantially the same period. In the following, the description is made where the objects are cell nuclei stained fluorescently.

As shown in FIG. 8, in the fluorescence image, there are cell nuclei with large fluorescence intensities (dark regions in the drawing) and cell nuclei with small fluorescence intensities (pale regions in the drawing), due to the ununiformity of the concentration of a fluorescence staining liquid or the differences between individual cell nuclei.

Further, in the fluorescence image, there are a cell nucleus having a perfect shape (in the drawing, regions in a circular shape or an elliptical shape), a cell nucleus that is divided into two (in the drawing, regions in a nearly semi-circular shape), and two cell nuclei that are in contact with each other or laid on each other to seemingly become one (in the drawing, regions in a shape in which two circular shapes or two elliptical shapes are partially overlapped with each other).

As described above, since the expression rate of fluorescence is varied between the individual cell nuclei, it is difficult to accurately determine the number of cell nuclei from the sum total of the fluorescence intensity. Further, since there are cell nuclei that seemingly become one and a cell nucleus that is divided, it is difficult to accurately estimate the number of cell nuclei even by counting the number of regions emitting fluorescence. When it is not enabled that the number of cell nuclei is accurately determined, it is also difficult to accurately determine the DNA amount.

On the other hand, the optical thickness image has a pixel value (an optical thickness) proportional to the concentration and thickness of a substance at each position. Therefore, in a case where substances contained in a region are all regarded as the same substance, the sum total of pixel values in the region is determined, and thus, the total amount of substances contained in the region can be known.

However, in the optical thickness image, since the type of substance is unknown, a substance other than a cell nucleus is possibly contained. In comparison of the fluorescence image (FIG. 8) with the optical thickness image (FIG. 9), since three regions indicated by arrows in the optical thickness image (FIG. 9) emit no fluorescence in the fluorescence image (FIG. 8), it is revealed that these regions do not express cell nuclei stained fluorescently. The cause of an object other than a cell nucleus appearing in the optical thickness image is, for example, the imperfect removal of an object other than a cell nucleus (for example, a cell organelle) in nuclear fraction work.

As described above, since the fluorescence image and the optical thickness image have problems, in a case where only one of the fluorescence image and the optical thickness image is used, it is difficult to accurately determine the number of cell nuclei in a sample.

In the present embodiment, both of the fluorescence image and the optical thickness image are used, and thus, the number of cell nuclei in a sample can be accurately determined, and further, the total amount of DNA in a sample can be accurately determined. That is, in the present embodiment, the specificity of the fluorescence image with respect to a fluorescent object is used, and thus, the problem of the optical thickness image relating to substance identification is solved, and the merit of quantitative determination of the optical thickness image is utilized.

Figure 10:
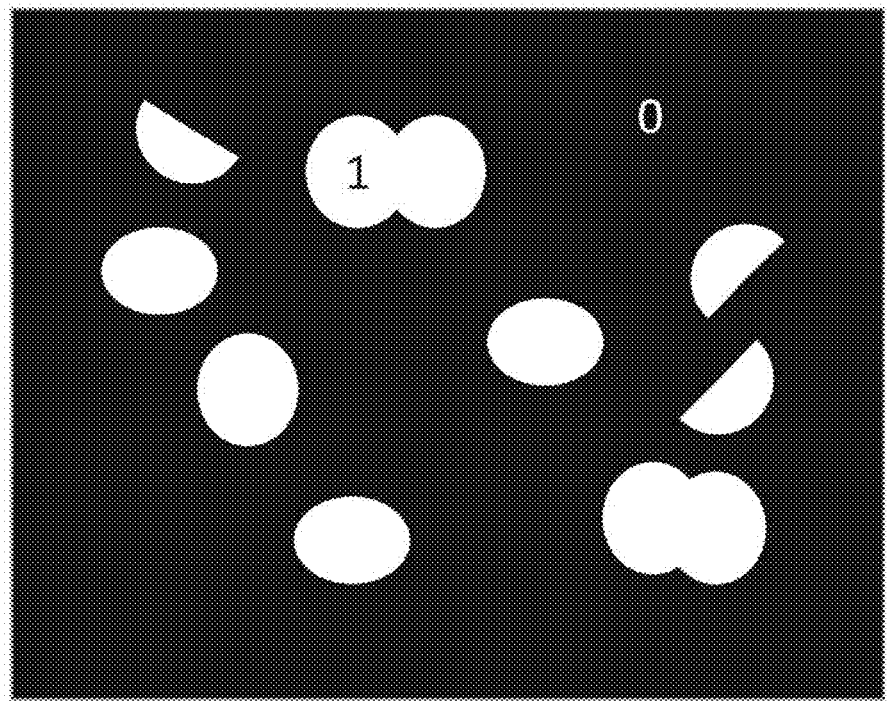
FIG. 10 is a diagram showing a mask image generated based on the fluorescence image (FIG. 8).

Although the fluorescence image is inferior at the point of quantitative determination, the fluorescence image has specificity for a fluorescent object. Therefore, the operation unit 4 can generate a mask image showing a region in which pixel values in the fluorescence image (FIG. 8) are larger than a threshold value. FIG. 10 is a diagram showing a mask image generated based on the fluorescence image (FIG. 8). The mask image (FIG. 10) is an image in which respective pixel values in the fluorescence image (FIG. 8) are binarized by an appropriate threshold value. In the mask image (FIG. 10), a white region is a region in which the pixel values of fluorescence are larger than the threshold value, that is, the region of cell nuclei emitting fluorescence. A black region is a region in which the pixel values of fluorescence are smaller than the threshold value. In the mask image (FIG. 10), the pixel values in the white region are set to 1, and the pixel values in the black region are set to 0.

Figure 11:
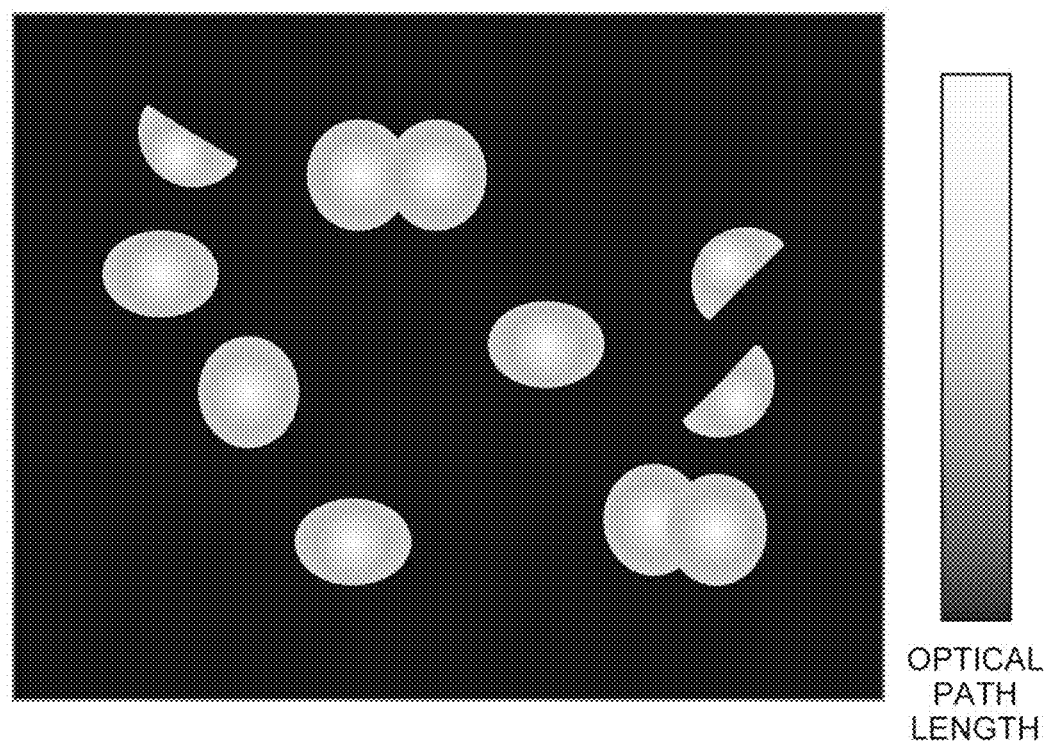
FIG. 11 is a diagram showing an image that is a product of the optical thickness image (FIG. 9) and the mask image (FIG. 10).

The optical thickness image (FIG. 9) is multiplied by the mask image (FIG. 10), and thus, the region (that is, the region of cell nucleus emitting fluorescence) shown by the mask image (FIG. 10) in the optical thickness image (FIG. 9) can be extracted. FIG. 11 is a diagram showing an image that is a product of the optical thickness image (FIG. 9) and the mask image (FIG. 10). In the product image (FIG. 11), objects other than cell nuclei present in the optical thickness image (FIG. 9) are removed, and only the cell nuclei present in the optical thickness image (FIG. 9) are shown.

The pixel value (the optical thickness) at each position in the product image (FIG. 11) is proportional to the concentration and thickness of the cell nucleus at that position. Therefore, the operation unit 4 integrates the pixel values in the product image (FIG. 11) entirely through the field of view. An integrated value $V_N$ thus obtained is an index proportional to the total amount of cell nuclei present in the field of view, and is also an index proportional to the total amount of DNA present in the field of view.

Since the measurement value of the optical thickness is a value with reproducibility, for example, the pixel values in the product image (FIG. 11) are integrated entirely through the field of view on a sample in which individual cell nuclei can be clearly distinguished and the number of cell nuclei can be clearly determined, the integrated value is divided by the number of cell nuclei in the field of view, and thus, the average integrated value $V_1$ per cell nucleus can be determined. The integrated value $V_N$ obtained by integrating the pixel values in the product image (FIG. 11) entirely through the field of view on the sample that is a measurement object is divided by the average integrated value $V_1$ per cell nucleus, and thus, the number of cell nuclei present in the field of view of the sample can be determined, and further, the total amount of DNA present in the field of view of the sample can be determined.

In addition, when the magnification in image acquisition is different, since the number of pixels in the field of view is different even in the same field of view, the integrated value of the pixel values entirely through the field of view is also different. Therefore, in a case where a magnification in image acquisition is different, the integrated value is corrected by the magnification. For example, the integrated value of the pixel values entirely through the field of view is divided by the number of pixels in the field of view, and thus, the value can be obtained, which is not dependent on the magnification in image acquisition.

Further, the field of view is not limited to one field of view, and may be a composite field of view in which a plurality of fields of view are combined. The number of cell nuclei can be similarly determined based on the fluorescence image and the interference image acquired in the composite field of view.

For example, in a case where the sample is a cell suspension, first, the cell membranes of cells in the sample are dissolved by nuclear fraction, and only cell nuclei are extracted. A liquid solution in which only cell nuclei thus extracted are mainly collected is injected into a container whose volume is known in advance. Assuming that the amount of the liquid solution in which only cell nuclei are collected is 1 mL, and a part of the sufficiently suspended liquid solution is injected into a container in a size of 10 mm×10 mm×1 mm (height), a 100 μL volume of the container corresponds to 1/10 of the original sample. In the sample placed in the container, a fluorescence image and an interference image are acquired in a field of view of 1 mm×1 mm. The sample amount included in this field of view corresponds to 1/1000 of the original sample.

Then, a mask image is generated from the fluorescence image, and an optical thickness image is generated from the interference image. Further, a product image is generated from the mask image and the optical thickness image, and the integrated value $V_N$ of the product image is determined. This integrated value $V_N$ is divided by an average integrated value $V_1$ per cell nucleus, and then the number of cell nuclei present in the field of view is determined. The number of cell nuclei in the field of view thus determined is multiplied by 1000, and thus, the number of cell nuclei contained in the original sample can be determined. The amount of DNA contained in one cell nucleus can be estimated, and thus, the total amount of DNA contained in the original sample can also be determined.

Compared with the conventional absorption method, in the present embodiment, the influence of light absorbing substances other than DNA on the measurement result is suppressed, and the influence of absorption of a liquid solution itself is suppressed even in the case of a liquid sample. Further, in the present embodiment, even a low concentration sample can be accurately measured.

Compared with the conventional fluorescence method, in the present embodiment, the influence of the uneven staining of fluorescence or variations in the expression rate of fluorescence on the measurement result is suppressed, and the influence of autofluorescence on the measurement result is also suppressed. Further, in the present embodiment, cell nuclei can be accurately measured even in a case where the concentration is very high and a plurality of cell nuclei are vertically overlapped, and even a low concentration sample in which autofluorescence or background fluorescence is non-negligible can be accurately measured.

Compared with the conventional method of counting stained cell nuclei, in the present embodiment, cell nuclei can be accurately measured even in a case where there are cell nuclei that seemingly become one or a cell nucleus that is divided. Further, in the present embodiment, since the segmentation process for demarcating the region of a cell nucleus is unnecessary, no error occurs due to the process, and a high-speed process can be performed.

The measurement apparatus and the measurement method are not limited to the embodiments and the configuration examples described above, and can be variously modified.

The measurement apparatus of the above embodiment is configured to include (1) a fluorescence image acquisition unit configured to acquire a fluorescence image including an object, (2) an interference image acquisition unit configured to acquire an interference image including the object, and (3) an operation unit configured to perform an operation of determining an integrated value of an optical thickness based on the interference image in a region in the interference image corresponding to a region in which pixel values in the fluorescence image are larger than a threshold value.

In the above measurement apparatus, the operation unit may be configured to generate an optical thickness image based on the interference image, generate a mask image showing the region in which the pixel values in the fluorescence image are larger than the threshold value, and determine the integrated value of the optical thickness in the region shown by the mask image in the optical thickness image.

In the above measurement apparatus, the interference image acquisition unit may be configured to acquire the interference image using incoherent light.

In the above measurement apparatus, at least parts of optical systems of the interference image acquisition unit and the fluorescence image acquisition unit may be configured in common.

The measurement method of the above embodiment is configured to include (1) a fluorescence image acquisition step of acquiring a fluorescence image including an object by a fluorescence image acquisition unit, (2) an interference image acquisition step of acquiring an interference image including the object by an interference image acquisition unit, and (3) an operation step of performing an operation of determining an integrated value of an optical thickness based on the interference image in a region in the interference image corresponding to a region in which pixel values in the fluorescence image are larger than a threshold value.

In the above measurement method, in the operation step, an optical thickness image may be generated based on the interference image, a mask image showing the region in which the pixel values in the fluorescence image are larger than the threshold value may be generated, and the integrated value of the optical thickness may be determined in the region shown by the mask image in the optical thickness image.

In the above measurement method, in the interference image acquisition step, the interference image acquisition unit may be configured to acquire the interference image using incoherent light.

In the above measurement method, at least parts of optical systems of the interference image acquisition unit and the fluorescence image acquisition unit may be configured in common.

In the above measurement method, the object may be a cell nucleus stained fluorescently, and in the operation step, the integrated value of the optical thickness may be determined as an index proportional to a total amount of cell nuclei.

The embodiments may be used as an apparatus and a method that can accurately measure the amount of object in a sample.

From the invention thus described, it will be obvious that the invention may be varied in many ways. Such variations are not to be regarded as a departure from the spirit and scope of the invention, and all such modifications as would be obvious to one skilled in the art are intended for inclusion within the scope of the following claims.

What is claimed is:
1. A measurement apparatus comprising:
   a fluorescence image acquisition unit configured to acquire a fluorescence image including an object;
   an interference image acquisition unit configured to acquire an interference image including the object; and
   an operation unit configured to perform an operation of deter mining an integrated value of an optical thickness based on the interference image, in a region in the interference image corresponding to a region in which pixel values in the fluorescence image are larger than a threshold value.
2. The measurement apparatus according to claim 1, wherein the operation unit is configured to generate an optical thickness image based on the interference image, generate a mask image showing the region in which the pixel values in the fluorescence image are larger than the threshold value, and determine the integrated value of the optical thickness in the region shown by the mask image in the optical thickness image.

3. The measurement apparatus according to claim 1, wherein the interference image acquisition unit is configured to acquire the interference image using incoherent light.

4. The measurement apparatus according to claim 1, wherein at least parts of optical systems of the interference image acquisition unit and the fluorescence image acquisition unit are configured in common.

5. A measurement method comprising:
   a fluorescence image acquisition step of acquiring a fluorescence image including an object by a fluorescence image acquisition unit;
   an interference image acquisition step of acquiring an interference image including the object by an interference image acquisition unit; and
   an operation step of performing an operation of determining an integrated value of an optical thickness based on the interference image, in a region in the interference image corresponding to a region in which pixel values in the fluorescence image are larger than a threshold value.

6. The measurement method according to claim 5, wherein, in the operation step, an optical thickness image is generated based on the interference image, a mask image showing the region in which the pixel values in the fluorescence image are larger than the threshold value is generated, and the integrated value of the optical thickness is determined in the region shown by the mask image in the optical thickness image.

7. The measurement method according to claim 5, wherein, in the interference image acquisition step, the interference image acquisition unit is configured to acquire the interference image using incoherent light.

8. The measurement method according to claim 5, wherein at least parts of optical systems of the interference image acquisition unit and the fluorescence image acquisition unit are configured in common.

9. The measurement method according to claim 5, wherein
   the object is a cell nucleus stained fluorescently, and
   in the operation step, the integrated value of the optical thickness is determined as an index proportional to a total amount of cell nuclei.

* * * * *